(12) United States Patent
Von Mentzer et al.

(10) Patent No.: US 10,118,921 B2
(45) Date of Patent: Nov. 6, 2018

(54) DIARYLMETHYLIDENE PIPERIDINE DERIVATIVES AND THEIR USE AS DELTA OPOID RECEPTOR AGNISTS

(71) Applicant: PHARMNOVO AB, Öckerö (SE)

(72) Inventors: Bengt Von Mentzer, Göteborg (SE); Ingemar Starke, Göteborg (SE); Peter Brandt, Uppsala (SE)

(73) Assignee: PHARMNOVO AB, Öckerö (SE)

( * ) Notice: Subject to any disclaimer, the term of this patent is extended or adjusted under 35 U.S.C. 154(b) by 0 days.

(21) Appl. No.: 15/535,464

(22) PCT Filed: Dec. 17, 2015

(86) PCT No.: PCT/SE2015/051363
§ 371 (c)(1),
(2) Date: Jun. 13, 2017

(87) PCT Pub. No.: WO2016/099393
PCT Pub. Date: Jun. 23, 2016

(65) Prior Publication Data
US 2017/0327491 A1    Nov. 16, 2017

(30) Foreign Application Priority Data
Dec. 19, 2014  (SE) ...................... 1451616

(51) Int. Cl.
*C07D 417/06*  (2006.01)
*C07D 401/06*  (2006.01)
*A61P 25/04*   (2006.01)

(52) U.S. Cl.
CPC ............ *C07D 417/06* (2013.01); *A61P 25/04* (2018.01); *C07D 401/06* (2013.01)

(58) Field of Classification Search
CPC .................................................. C07D 417/06
USPC ........................................ 546/209; 514/326
See application file for complete search history.

(56) References Cited

FOREIGN PATENT DOCUMENTS

| WO | 02094784   | 11/2002 |
|----|------------|---------|
| WO | 03029215   | 4/2003  |
| WO | 2004087663 | 10/2004 |
| WO | 2004101520 | 11/2004 |

OTHER PUBLICATIONS

International Search Report issued in parent international application No. PCT/SE2015/051363, dated May 4, 2016, pp. 1-3.
International Preliminary Report on Patentability and Written Opinion issued in parent international application No. PCT/SE2015/051363, dated May 4, 2016, pp. 1-8.

*Primary Examiner* — Patricia L Morris
(74) *Attorney, Agent, or Firm* — Jeffrey S. Melcher; Manelli Selter PLLC

(57) ABSTRACT

A compound of formula I, for use in pain therapy and a pharmaceutical composition comprising said compound.

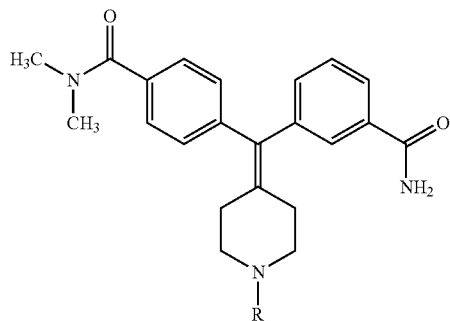

13 Claims, No Drawings

DIARYLMETHYLIDENE PIPERIDINE DERIVATIVES AND THEIR USE AS DELTA OPOID RECEPTOR AGNISTS

FIELD OF INVENTION

The present invention is directed to novel compounds, to a process for their preparation, their use and pharmaceutical compositions comprising the novel compounds. The novel selective δ-opioid receptor agonists are useful in therapy, and in particular for the treatment of pain, anxiety and depression.

BACKGROUND OF INVENTION

Delta opioid receptors (DORs) have been considered as a potential target to relieve pain conditions and depression and anxiety disorders. Physical pain is a typical sensory experience that may be described as the unpleasant awareness of a noxious stimulus or bodily harm. Individuals experience pain by various daily hurts and aches, and sometimes through more serious injuries or illnesses. For scientific and clinical purposes, pain is defined by the International Association for the Study of Pain (IASP) as "an unpleasant sensory and emotional experience associated with actual or potential tissue damage, or described in terms of such damage".

Pain is a common reason for physician consultation. It is a major symptom in many medical conditions, significantly interfering with a person's quality of life and general functioning. Diagnosis is based on characterizing pain in various ways, according to duration, intensity, type (dull, burning, throbbing or stabbing), source, or location in body. Usually pain stops without treatment or responds to simple measures such as resting or taking an analgesic, and it is then called 'acute' pain. But it may also become intractable and develop into a condition called chronic pain, in which pain is no longer considered a symptom but an illness by itself.

Pain is the most common symptom for which patients seek medical advice and treatment. Pain can be acute or chronic. While acute pain is usually self-limited, chronic pain can persist for 3 months or longer and lead to significant changes in a patient's personality, lifestyle, functional ability or overall quality of life (K. M. Foley, Pain, in Cecil Textbook of Medicine 100-107, J. C. Bennett and F. Plum eds., 20th ed. 1996).

Current analgesic therapies are only poorly effective and are associated with significant side effects, especially concerning chronic conditions.

The impact of chronic pain can vary from mild discomfort to the worst pain imaginable, having a devastating effect on the sufferers and their families. The types of pain are many and varied and include lower back pain, arthritis (especially osteoarthritis), headache (including migraine), fibromyalgia, nerve damage (neuropathy), neurological disease (e.g. multiple sclerosis), and post-viral illness (e.g. shingles).

Other CNS-related diseases such as Alzheimer's and Parkinson's have a high prevalence of associated pain. The incidence of chronic pain increases with advancing and is associated with and potentiated by depressive illness and loss of sleep.

DORs have multiple roles in the central nervous system disorders beside pain, such as in depression, anxiety, epilepsy, and stress and in gastrointestinal disorders such as in diarrhea, postoperative ileus, ulceration and irritable bowel syndrome and in related inflammatory disorders such as in osteoarthritis and rheumatoid arthritis, and in others including respiratory, alcoholism and obesity/binge eating.

The identification of at least three different populations of opioid receptors (δ), (μ) and (κ) receptors is now well established and all three are apparent in both central and peripheral nervous systems of many species including man.

A recent survey of more than 45,000 people in 16 countries revealed that almost 1 in 5 of the European population suffers moderate or severe pain persisting for more than 6 months. Chronic pain, therefore, constitutes an enormous burden on national economies and patients' quality of life. Given the number of different chronic pain states, the patient population is extremely varied, although it is very likely to be skewed towards the upper age range with neuropathies and joint pain being particularly prominent. In institutionalized elderly patients for example, up to 80% report a current pain problem although a significant proportion receive inadequate analgesic therapy. There is, therefore, an urgent need for novel pain therapies that are effective over prolonged periods with low side-effect risk.

The commonly used opioids, such as, codeine, dihydrocodeine (for mild to moderate pain) and oxycodone, tramadol etc. (for severe pain) are either non-selective, acting on all three opioid receptor sub-types or somewhat μ receptor-biased and they produce the full range of both beneficial and unwanted effects.

The widespread distribution of opioid receptor subtypes in the CNS and peripheral tissues results in the associated side-effects of nausea, constipation, itching and danger of life-threatening respiratory depression, produced by mixed opioid ligands. The development of tolerance additionally limits their clinical efficacy.

The development of tolerance additionally limits their clinical efficacy. Meta-analysis-derived evidence regarding the clinical efficacy of traditional opioids and other commonly used analgesics in chronic pain states is weak or negative; amitriptyline (a first line analgesic for neuropathic pain) benefits less than 40% of patients and, only about one third of patients treated with gabapentin obtain significant relief. The currently available voltage-activated sodium channel blockers also have very limited efficacy and significant CNS and cardio toxicity risks.

This commonality offers the possibility that modifying the activity of individual targets, such as the δ-opioid receptor (DOR) will provide benefit in pain treatment.

Outline of Invention

Compounds of this invention show selective high potency for the DOR. Compounds of the invention deliver a widened therapeutic window, and have the potential, in contrast to existing analgesics delivering only moderate pain relief, to produce maintained analgesia in pain states with less risk of unwanted effects including respiratory depression and constipation.

Compounds of this invention will significantly expand treatment options for clinicians and increase the quality of life for a huge number of patients.

The present invention provides a compound of formula (I)

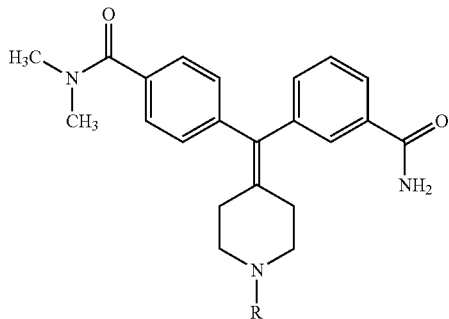

(I)

or pharmaceutically acceptable salts thereof
Wherein
R is selected from any one of

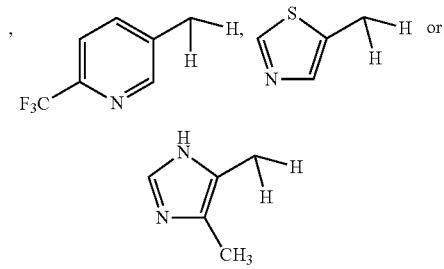

According to an aspect of the invention, a compound of formula I is

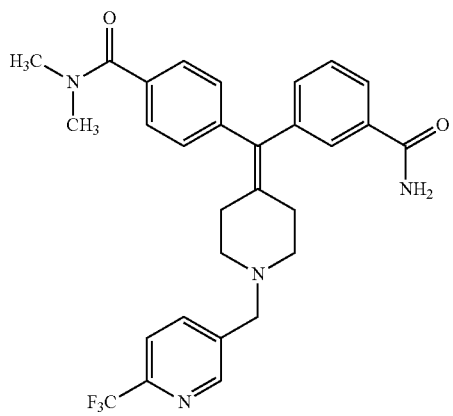

Ia

According to another aspect of the invention, a compound of formula I is

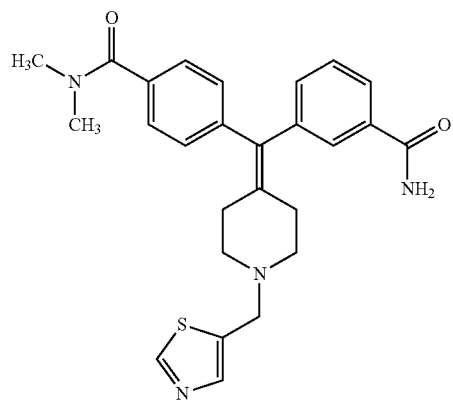 [SMILES: CN(C)C(=O)c1ccc(C(=C2CCN(Cc3cncs3)CC2)c2cccc(C(N)=O)c2)cc1]

Ib

According to another aspect of the invention, a compound of formula I is

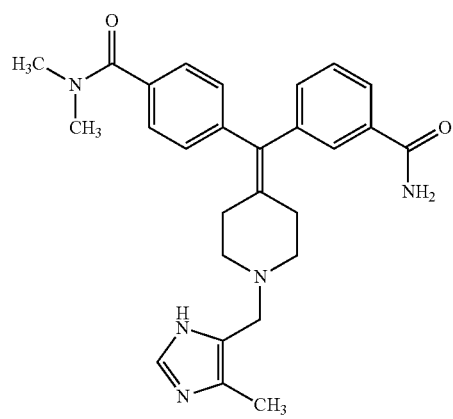

Ic

According to an aspect of the invention the compounds of formula I are used in pain therapy, such as treating acute pain and chronic pain.

Compounds of the invention are highly potent and will retain analgesic potency on repeated administration. Compounds of the invention will be useful in therapy, especially for the treatment of various pain conditions such as chronic pain, neuropathic pain, acute pain, cancer pain, pain caused by rheumatoid arthritis, osteoarthritis, fibromyalgia, migraine, visceral pain, diabetic pain etc.

Compounds of the invention are equally useful for the treatment of depression and anxiety as for various types of pain conditions, as mentioned above.

Compounds of the invention are useful for the treatment of urinary incontinence, various mental illnesses, cough, lung edema, various gastro-intestinal disorders (irritable bowel syndrome, irritable bowel disease), spinal injury and drug addiction, including the treatment of alcohol, nicotine, opioid and other drug abuse and for disorders of the sympathetic nervous system for example hypertension.

Compounds of the invention are useful as immunomodulators, especially for autoimmune diseases, such as arthritis, for skin grafts and organ transplants.

Compounds of the invention are useful in disease states where degeneration or dysfunction of opioid receptors is present or implicated in that paradigm. This may involve the use of isotopically labeled versions of the compounds of the invention in diagnostic techniques and imaging applications such as positron emission tomography (PET).

Compounds of the invention are useful as an analgesic agent for use during general anesthesia and monitored anesthesia care. Combinations of agents with different properties are often used to achieve a balance of effects needed to maintain the anesthetic state (e.g. amnesia, analgesia, muscle relaxation and sedation). Included in this combination are inhaled anesthetics, hypnotics, anxiolytics, neuromuscular blockers, neuropeptide receptor blockers and other opioids.

Compounds of the invention can be used in combination therapy with other pain effective compounds.

Within the scope of the invention is the use of the compound of formula I above, for the manufacture of a medicament for the treatment of any of the conditions discussed above.

A further aspect of the invention is a method for the treatment of a subject suffering from any of the conditions discussed above, whereby an effective amount of compound according to the formula I above, is administered to a patient in need of such treatment.

A further aspect of the invention is a pharmaceutical composition comprising at least a compound of the formula I as an active ingredient, or a physiologically acceptable salt thereof together with a pharmaceutically acceptable carrier.

Methods of Preparation

The compounds of formula (I) prepared as outlined in scheme 1.

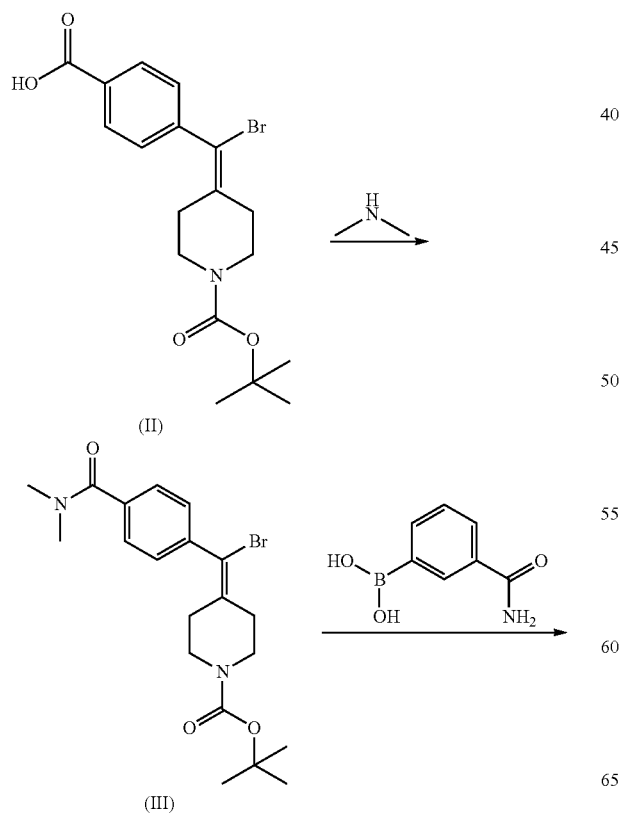

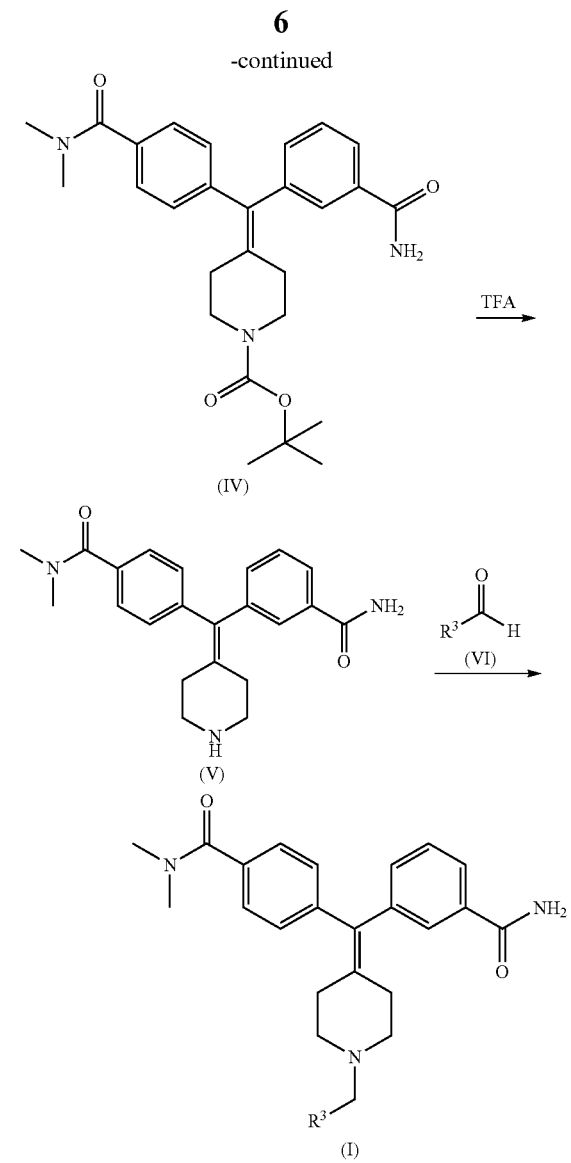

Wherein R'CH=O is:

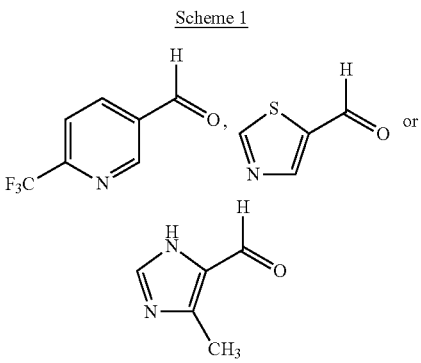

The following abbreviations have been used:

Dppf=(diphenylphosphino)ferrocene
HATU=1-[Bis(dimethylamino)methylene]-1H-1,2,3-triazolo[4,5-b]pyridinium-3-oxid hexafluorophosphate

EXAMPLES

The invention is illustrated by the following examples;

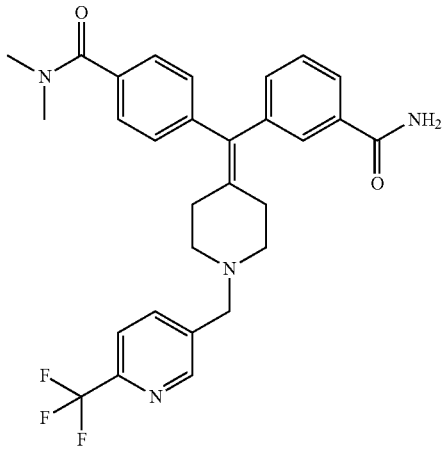

Ia

Example Ia. 4-[(3-Carbamoylphenyl)(1-{[6-(trifluoromethyl)pyridin-3-yl]methyl}piperidin-4-ylidene)methyl]-N,N-dimethylbenzamide 4-[(3-Carbamoylphenyl)(piperidin-4-ylidene)methyl]-N,N-dimethylbenzamide (40 mg, 11 mmol) and 6-(trifluoromethyl)pyridine-3-carbaldehyde (21.2 mg, 0.12 mmol) were dissolved in dichloroethane (1.5 mL). Acetic acid (6.3 µL, 0.11 mmol) was added and the reaction was stirred for 10 minutes at room temperature before NaBH(OAc)$_3$ (37.3 mg, 0.18 mmol) was added. The reaction mixture was stirred at room temperature for 2 days. Methylene chloride (1 mL) was added and the mixture was washed with water (1 mL). The water phase was extracted with methylene chloride (1 mL×3). The combined organic phases were dried with Na$_2$SO$_4$, filtered and evaporated. The crude product was purified by preparative HPLC (30 to 65% CH$_3$CN in 50 mM NH$_4$HCO$_{3(aq)}$) to give the title compound (19.0 mg, 33% yield) as a light yellow solid. MS ESI$^+$ m/z 523 [M+H]$^+$.

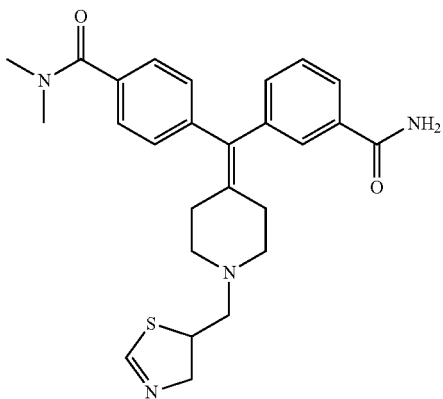

Ib

Example Ib. 4-[(3-Carbamoylphenyl)[1-(1,3-thiazol-5-ylmethyl)piperidin-4-ylidene]methyl]-N,N-dimethylbenzamide 4-[(3-Carbamoylphenyl)(piperidin-4-ylidene)methyl]-N,N-dimethylbenzamide (40 mg, 11 mmol) and 1,3-thiazole-5-carbaldehyde (13.7 mg, 0.12 mmol) were dissolved in dichloroethane (1.5 mL). Acetic acid (6.3 µL, 0.11 mmol) was added and the reaction was stirred for 10 minutes at room temperature before NaBH(OAc)$_3$ (37.3 mg, 0.18 mmol) was added. The reaction mixture was stirred at room temperature for 2 days. Methylene chloride (1 mL) was added and the mixture was washed with water (1 mL). The water phase was extracted with methylene chloride (1 mL×3). The combined organic phases were dried with Na$_2$SO$_4$, filtered and evaporated. The crude product was purified by preparative HPLC (25 to 65% CH$_3$CN in 50 mM NH$_4$HCO$_{3(aq)}$) to give the title compound (8.2 mg, 16% yield) as a white solid. MS ESI$^+$ m/z 461 [M+H]$^+$.

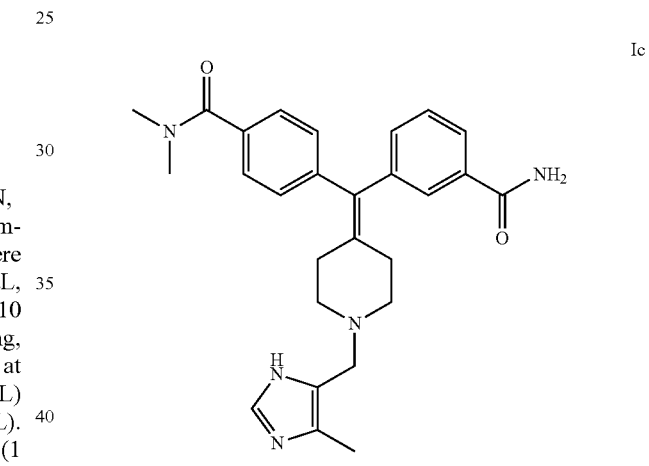

Ic

Example Ic. 4-[(3-Carbamoylphenyl)({1-[(4-methyl-1H-imidazol-5-yl)methyl]piperidin-4-ylidene})methyl]-N,N-dimethylbenzamide 4-[(3-Carbamoylphenyl)(piperidin-4-ylidene)methyl]-N,N-dimethylbenzamide (40 mg, 11 mmol) and 4-methyl-1H-imidazole-5-carbaldehyde (13.3 mg, 0.12 mmol) were dissolved in dichloroethane (1.5 mL). Acetic acid (6.3 µL, 0.11 mmol) was added and the reaction was stirred for 10 minutes at room temperature before NaBH(OAc)$_3$ (37.3 mg, 0.18 mmol) was added. The reaction mixture was stirred at room temperature for 2 days. Methylene chloride (1 mL) was added and the mixture was washed with water (1 mL). The water phase was extracted with methylene chloride (1 mL×3). The combined organic phases were dried with Na$_2$SO$_4$, filtered and evaporated. The crude product was purified by preparative HPLC (10 to 50% CH$_3$CN in 50 mM NH$_4$HCO$_{3(aq)}$) to give the title compound (14 mg, 28% yield) as a white solid. MS ESI$^+$ m/z 458 [M+H]$^+$.

Preparation of Intermediates

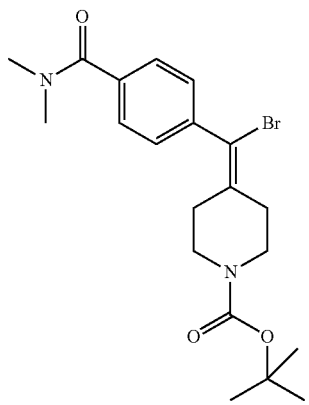

Example III. tert-Butyl 4-(bromo[4-(dimethylcarbamoyl)phenyl]methylidene)piperidine-1-carboxylate To 4-({1-[(tert-butoxy)carbonyl]piperidin-4-ylidene}(3-carbamoylphenyl)methyl)benzoic acid (1.00 g, 2.52 mmol) in DMF (8.0 mL) were added HATU (1.15 g, 3.02 mmol) and N,N-diisopropylethylamine (1.8 mL, 10.1 mmol) and the reaction was stirred for 6 min at room temperature. Then dimethylamine-HCl (0.617 g, 7.57 mmol) was added and the reaction was stirred at room temperature overnight. Ethyl acetate was added and the solution was washed with ice-cooled 1 M HCl, NaHCO$_3$ (sat. aq.) and brine, dried (Na$_2$SO$_4$), filtered and concentrated to give 1.33 g of the crude product which was taken to the next step, without further purification. MS ESI$^+$ m/z 367 [M+H]$^+$-t-Bu.

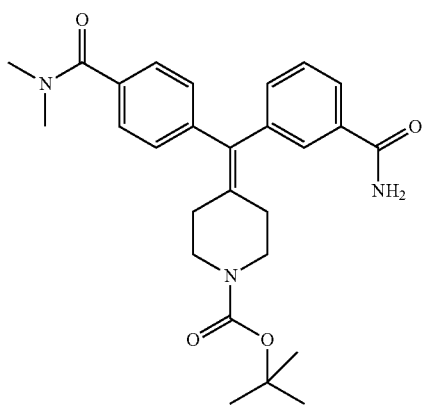

Example IV. tert-Butyl 4-[(3carbamoylphenyl)[4-(dimethylcarbamoyl) phenyl]methylidene]piperidine-1-carboxylate tert-Butyl 4-{bromo[4-(dimethylcarbamoyl)phenyl]methylidene}piperidine-1-carboxylate (0.533 g, 1.26 mmol) and (3-carbamoylphenyl)boronic acid (0.249 g, 1.51 mmol) were dissolved in dimethoxyethane (17 mL) and 2 M K$_2$CO$_3$ (aq) (0.6 mL) and PdCl$_2$(dppf) (0.051 g, 0.063 mmol) were added under nitrogen and the reaction was heated at 80° C. for 3.5 h. The reaction was cooled to room temperature and left over weekend. Methylene chloride and water were added and the phases were separated. The aqueous phase was extracted with methylene chloride (3×). The combined phases were washed with brine, dried (MgSO$_4$), filtered and concentrated to give 0.630 g of the crude product, a brown oil, which was taken to the next step without further purification. MS ESI$^+$ m/z 408 [M+H]$^+$-t-Bu.

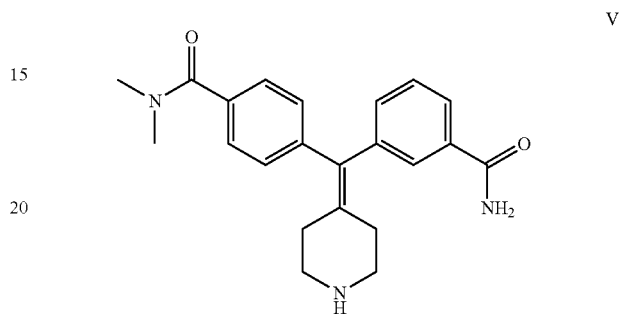

Example V. 4-[(3-Carbamoylphenyl)(piperidin-4-ylidene)methyl]-N,N-dimethylbenzamide tert-Butyl 4-[(3-carbamoylphenyl)[4-(dimethylcarbamoyl)phenyl]methylidene]piperidine-1-carboxylate (0.630 g, 1.36 mmol) was dissolved in methylene chloride (3 mL) and a mixture of trifluoroacetic acid/methylene chloride (3.5 mL) was added. The reaction was stirred at room temperature for 1 h 15 min. The reaction mixture was evaporated and the residue was redissolved in methylene chloride. The organic phase was washed with sat aq K$_2$CO$_3$ (2×), dried (MgSO$_4$), filtered and concentrated to give 0.550 g of the crude product as a brown oil which was taken to the next step, without further purification. MS ESI$^+$ m/z 364 [M+H]$^+$.

Pharmaceutical Compositions

There is provided a method for treatment of a condition which method comprises administration of a therapeutically effective amount of the compound of formula I to a person suffering from, or susceptible to, such a condition. The compounds of the invention will normally be administered via the oral, topical, parenteral, intravenous, intramuscular, subcutaneous, intra articular injection, or in other injectable ways, buccal, sublingual, rectal, vaginal, transdermal and/or nasal route and/or via inhalation, in the form of pharmaceutical preparations comprising the active ingredient or a pharmaceutically acceptable salt thereof, in a pharmaceutically acceptable dosage form. Depending upon the disorder and patient to be treated and the route of administration, the compositions may be administered at varying doses.

Suitable daily doses of the compounds of the invention in therapeutically treatment of humans are about 0.0001-100 mg/kg body weight, preferably 0.01-10 mg/kg body weight.

Oral formulations are tablets or capsules which may be formulated by methods known to those skilled in the art to provide doses of the active compound in the range of 0.007 mg to 700 mg for example 1 mg, 3 mg, 5 mg, 10 mg, 25 mg, 50 mg, 100 mg, 250, and 500 mg.

The optimum dosage and frequency of administration will depend on the particular condition being treated and its severity; the species of the patient; the age, sex, size and weight, diet, and general physical condition of the particular patient; brain/body weight ratio; other medication the patient may be taking; the route of administration; the formulation; and various other factors known to physicians and others skilled in the art.

According to a further aspect of the invention there is thus provided a pharmaceutical formulation including any of the compounds of the invention, or pharmaceutically acceptable derivatives thereof, in admixture with pharmaceutically acceptable adjuvants, diluents and/or carriers.

The compounds of the invention may be present in the pharmaceutical formulation in a concentration from 0.1 to 99.5%, such as from 0.5 to 95%, by weight of the total formulation.

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the above-mentioned excipients for tablets. Also liquid or semi-solid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain coloring agents, flavoring agents, saccharine and/or carboxymethylcellulose as a thickening agent or other excipients known to those skilled in art.

Biological Evaluation

In Vitro

δ-opioid receptors (DOR) are coupled to inhibitory G proteins (Gi/o) which inhibit adenylyl cyclase activity, open K$^+$ channels and block Ca$^{2+}$ channels. They can also couple, in an agonist-dependent manner to β-arrestin 2, which lead to desensitization, and to MAP kinase (ERK) phosphorylation.

In Vitro Assessment of δ-Opioid Agonist Potency: In Vitro Assessment of δ-Opioid Agonist Potency:

cAMP measurements will be made in δ-opioid-expressing CHO cells exposed to increasing agonist concentrations using DiscoveRx cAMP Hunter™ assay kits. β-arrestin recruitment will be measured in the presence of increasing agonist concentrations using DiscoveRx Pathunter® kits. Selectivity of mu- and kappa-opioid receptors will be performed using Cerep cAMP evaluation from ref. 1392 and 2071 (Cerep Le Bois l'Evéque, 86600 Celle l'Evescault, France).

| Example | EC-50 cAMP (nM) | EC-50 beta-arrestin (nM) | Selectivity (mu/delta) | Selectivity (kappa/delta) |
|---|---|---|---|---|
| 1a | 2.8 | 28 | 360 | 360 |
| 1b | 0.5 | 4 | 100000 | 1000 |
| 1c | 0.5 | 3 | 1000 | 1000 |

In Vivo

Chronic Pain, Seltzer Model

The Seltzer assessment is used to evaluate chronic pain. Thirty male CD1 mice (29-37 g) are included in the study. They were obtained from Charles-River Ltd. and kept in the Animal Facility of the Department of Pharmacology and Pharmacotherapy at the University of Pécs at 24-25° C. provided with standard chow and water ad libitum. All experimental procedures are carried out according to the 1998/XXVIII Act of the Hungarian Parliament on Animal Protection and Consideration Decree of Scientific Procedures of Animal Experiments (243/1988) and complied with the recommendations of the Helsinki Declaration. The studies are approved by the Ethics Committee on Animal Research of Pécs University according to the Ethical Codex of Animal Experiments and license was given (license No.: BA 02/2000-11-2006). After a conditioning measurement three reliable control mechano-nociceptive thresholds are determined on three consecutive days for all mice and the operation is performed afterwards. On the 7$^{th}$ day following the nerve ligation the mechano-nociceptive thresholds are determined directly before and 15 min after i.p. drug administration to observe the difference between pre-injection and post-injection thresholds. Only mice with a minimum of 30% pre-injection hyperalgesia are included in the study.

The blood and the brain samples are taken 60 min after drug administration under deep ketamin-xylazine anesthesia and sent for further analysis. Blood (0.5-1.5 ml) is taken by cardiac puncture to EDTA-containing tubes and centrifuged. The plasma samples are stored at −70° C. The whole brain with the cerebellum and the brainstem is dissected, put into Eppendorf tubes, immediately frozen in liquid nitrogen and they are stored at −70° C.

Chronic Pain MNX OA Model

Rats are anaesthetized using 2.5% Isoflurane (Abbott, Maidenhead, UK) in oxygen with a flow rate of 1 L per minute. The left leg is shaved and surgically prepared. The medial collateral ligament is exposed and a section of it removed to expose the meniscus. The meniscus is cut through its full thickness at the narrowest point. The connective tissue layer and skin are then closed with coated Vicryl 8-0 and 4-0 sutures, respectively (Ethicon, Livingstone, UK). No post-operative analgesic drug is administered as pain behavior is an outcome measure of the experiment. Sham operated animals undergo an identical procedure with the exception that the meniscus is not transected. Effects of treatments on weight distribution through the left (ipsilateral) and right (contralateral) knees are assessed using an incapacitance meter (Linton Instruments UK). The change in hind paw weight distribution is defined as the difference in the amount of weight between the right contralateral control limb and the left ipsilateral treated limb divided by the sum of the weight right and left limbs×100. Hind paw withdrawal thresholds to mechanical stimulation are measured using calibrated von Frey monofilaments using the up down method. The animals are habituated on at least two occasions before commencement of the experiments. Baseline behavioral pain measurements are made at day 0 prior to model induction and then at day 14, 28, 35, and 49 days.

Acute Carrageenan-Induced Inflammatory Pain

λ-carrageenan (100 μL 2% in saline; Sigma, Poole, UK) is injected into the plantar surface of the rat hind paw. Mechanical stimuli (8-100 g von Frey monofilaments) are applied (in ascending order) to the peripheral receptive field at 10-min intervals, for 180 min, following injection of carrageenan and withdrawal responses recorded. Hind paw circumference is measured using suture looped around the paw at metatarsal level and gently tightened. The thread is then opened out and measured to the nearest millimeter. Measurements are taken prior to carrageenan injection and then at 60-min intervals thereafter.

Behavioral Studies

Rotarod

Co-ordination (Rotarod); the rotarod assessment is used to evaluate general co-ordinator behavior. It will be assessed by performance on the rotarod apparatus (Ugo Basile) on which mice will be trained for 3 days, each mouse receiving four training trials per day consisting of placing the mice for 2 min on a rod rotating at a speed of up to 24 rpm, the latency to fall off the rotarod onto foam rubber padding being measured with the trial terminating after 2 min if the mouse has not fallen off.

Open Field

Open field behavior; the open field assessment is use to evaluate general social behavior. Animals will be placed within a standard 'open field arena' and behavior monitored by computer tracking (Ethovision) for up to 2 hours per day. Overall locomotion will be measured and the time spent in the central part of the arena and in rearing will give an indication of anxiety-like behavior.

The invention claimed is:

1. A compound of formula I

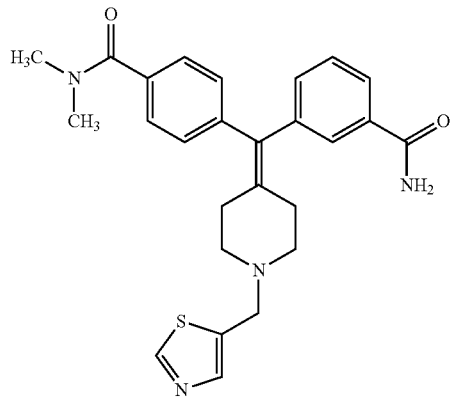

or a pharmaceutically acceptable salt thereof.

2. A method for treating a pain condition in a patient in need thereof comprising administering a therapeutically effective amount of the compound of formula I or a pharmaceutically acceptable salt thereof according to claim 1 to the patient to treat the pain condition.

3. The method according to claim 2, wherein the pain condition is directed towards acute pain.

4. The method according to claim 2, wherein the pain condition is directed towards chronic pain.

5. The method according to claim 4, wherein the pain condition is directed towards chronic joint pain.

6. The method according to claim 4, wherein the pain condition is directed towards chronic joint pain caused by osteoarthritis or fibromyalgia.

7. A pharmaceutical composition comprising at least a therapeutically effective amount of the compound of the formula I or a pharmaceutically acceptable salt thereof according to claim 1 as an active ingredient together with a pharmaceutically acceptable carrier.

8. A method for treating pain comprising the step of administering the composition according to claim 7 to a patient in need thereof to treat pain.

9. The method according to claim 8, wherein the pain is acute or chronic pain.

10. The method according to claim 8, wherein the pain is chronic joint pain.

11. The method according to claim 8, wherein composition is administered via at least one of oral, topical, parenteral, intravenous, intramuscular, subcutaneous, intra articular injection, buccal, sublingual, rectal, vaginal, transdermal, nasal or inhalation.

12. The method of claim 8, wherein the therapeutically effective amount of compound of the formula I or physiologically acceptable salt thereof is from 0.0001-100 mg/kg body weight of the patient.

13. The method of claim 8, wherein the therapeutically effective amount of compound of the formula I or physiologically acceptable salt thereof is from 0.01-10 mg/kg body weight of the patient.

* * * * *